United States Patent
de Ferra et al.

[11] Patent Number: 5,433,833
[45] Date of Patent: Jul. 18, 1995

[54] PROCESS FOR THE PREPARATION OF GLYCEROPHOSPHOLIPIDS

[75] Inventors: Lorenzo de Ferra; Sandra Rondinini; Patrizia R. Mussini; Fausto Bonifacio; Pietro Massardo; Oreste Piccolo, all of Patrica, Italy

[73] Assignee: Italfarmaco Sud S.p.A., Patrica, Italy

[21] Appl. No.: 240,469

[22] Filed: May 10, 1994

[30] Foreign Application Priority Data

May 11, 1993 [IT] Italy .................. MI93A0955

[51] Int. Cl.$^6$ .................. B01D 61/44
[52] U.S. Cl. .................. 204/182.4; 204/72; 205/50
[58] Field of Search .................. 204/72, 182.4; 205/50

[56] References Cited

U.S. PATENT DOCUMENTS 5,268,079 12/1993 Ochoa Gomez et al. ....... 204/182.4

FOREIGN PATENT DOCUMENTS 4218399 9/1993 Germany .

*Primary Examiner*—John Niebling
*Assistant Examiner*—Edna Wong
*Attorney, Agent, or Firm*—Oblon, Spivak, McClelland, Maier & Neustadt

[57] ABSTRACT

A process for fractionating deacylated glycerophospholipids of the formula (I):

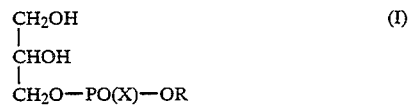

wherein R is a negative charge; a hydrogen atom; a $CH_2CH_2NR^1R^2$ residue wherein $R^1$ and $R^2$, which are the same or different, are H or $C_1$-$C_4$ alkyl; a $CH_2CH_2N^+(CH_3)_3$ residue; a $CH_2CH(NH_2)COOH$ residue or a residue of the formula:

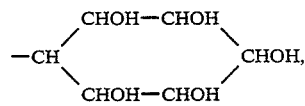

and X is OH or O$^-$, is described. The process involves subjecting an aqueous or hydroalcoholic mixture of two or more of the deacylated glycerophospholipids to electrodialysis in an electrolytic cell comprising a number of compartments. The compartments are separated by cation-exchange membranes, anion-exchange membranes or both cation-exchange and anion-exchange membranes, at a pH effective to differentiate the deacylated glycerophospholipids.

8 Claims, No Drawings

PROCESS FOR THE PREPARATION OF GLYCEROPHOSPHOLIPIDS

BACKGROUND OF THE INVENTION

The present invention refers to a new process for the fractionation of deacylated glycerophospholipids of the formula (I)

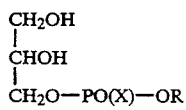

wherein

R is a negative charge, a hydrogen atom, a $CH_2CH_2NR^1R^2$ residue (wherein $R^1$ and $R^2$, which are the same or different, are H or $C_1$-$C_4$ alkyl), a $CH_2CH_2N^+(CH_3)_3$ residue, a $CH_2CH(NH_2)COOH$ residue or a residue of the formula

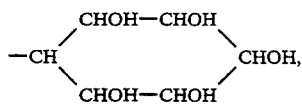

and X is OH or $O^-$, starting from aqueous or hydroalcoholic mixtures, having two or more components, of said deacylated glycerophospholipids and of possible impurities of a non-glycerophospholipidic kind.

The process is characterized in that said mixtures are subjected to electrodialysis in electrolytic cells having a number of compartments, separated by cation exchange and/or anion-exchange membranes, in pH conditions suited to differentiate, depending on the positive, negative or neutral charge, the deacylated glycerophospholipids to be separated or other impurities of a non-glycerophospholipidic kind.

In the following description, the following abbreviations will be used:
GPA for the compound of formula (I) wherein R=H;
GPE for the compound of formula (I) wherein R=$CH_2CH_2NH_2$;
GPC for the compound of formula (I) wherein R=$CH_2CH_2N^+(CH_3)_3$;
GPS for the compound of formula (I) wherein R=$CH_2CH(NH_2)COOH$;
GPI for the compound of formula (I) wherein R is a myoinositol residue.

The compounds (I) may be of a fully synthetic origin or they may be obtained by deacylation, according to known methods, of acylated phospholipids of vegetal origin (e.g. soy lecithin) or of animal origin (e.g. egg yolk or bovine brain). In both instances, in the mixture of compounds (I) to be subjected to electrodialysis, impurities of a non-glycerophospholipidic kind can be present, which may be removed during the fractionation process or subsequently according to conventional techniques, such as crystallization, liquid/liquid extraction or chromatography.

The process surprisingly attains an effective fractionation of the compounds (I) using, in comparison with known methods, smaller amounts of chemical reagents or solvents, giving smaller amounts of waste to be disposed of, allowing to obtain compounds (I) with higher productivity.

Compounds (I) are characterized in that they may be positively or negatively charged or they may be electrically neutral according to the pH value of the solution. For instance, GPC is positively charged at pH values <1 and amphotheric at pH values higher than 4, whereas GPE is positively charged at pH values <1, amphotheric in the pH range from 5 to about 8 and negatively charged at pH values >10. Similarly, such pH values of the solution can be found as to differentiate the species (I) in the mixture by means of the positive, negative or neutral charge. By the same method, it is possible to separate the compounds (I) from any other possible impurities in the starting mixtures.

Therefore, if a mixture of compounds (I), in aqueous or hydroalcoholic solution, is introduced at a suitable pH in a compartment of the electrolytic cell (hereinafter defined as compartment A), delimited by cation-exchange membranes and/or anion-exchange membranes, and an electrical potential is applied through the cell, it is possible to cause the migration of the negatively charged species to the anode through the anion-exchange membrane (having fixed positive charges and hereinafter referred to as $M^+$) in an adjacent compartment (hereinafter referred to as compartment B), whereas the positively charged species migrate to the cathode through the cation-exchange membrane (having fixed negative charges and hereinafter referred to as $M^-$) in an adjacent compartment (hereinafter referred to as compartment C) and leaving in compartment A the electrically neutral species.

According to the kind of mixture to be fractionated it is possible to carry out the separation working sequentially at different pH values.

The basic scheme of the cell, formed of a number of compartments, depends on the kind of mixture to be separated; in any case the electrodes, cathode and anode are present, in contact with electrolytic solutions of salts and/or inorganic acids or bases, respectively referred to as catholyte and anolyte, having a suitable composition and concentration compatible with the requirements of electrodic and fractionation processes. In compartments A, B and/or C, inorganic salts may also be present from the beginning or they may be subsequently added in order to increase conductivity whenever the presence of the charged species (I) would not be sufficient. The nature of the catholyte and anolyte is connected with that of the said inorganic salts, or to the kind of mixture of compounds (I) present in compartments A, B and C. The inorganic salts, acids or bases in the cell are dissociated in cations and anions and they may cross in their turn the membranes having opposite charge and they are repelled by the membranes having the same charge, competing in transport with the charged species (I). The compartments separated by the cationic and/or anionic membranes are in sufficient number to allow the introduction of the mixture of compounds (I) and the recovery of the fractionated species; the basic scheme may be repeated in series to increase the process productivity by connecting compartments of the same kind together.

For instance, cells of the following composition may be used:

1) (−)cathode/catholyte/$M^-$/compartment A/$M^+$/compartment B/$M^-$/anolyte/anode (+)
2) (−)cathode/catholyte/$M^+$/compartment C/$M^-$/compartment A/$M^+$/anolyte/anode (+)

3) (−)cathode/catholyte/M+/compartment
C/M−/compartment A/M+/compartment
B/M−/anolyte/anode (+)

4) (−)cathode/catholyte/M+/compartment A/M+-
/compartment B/M/anolyte/anode (+)

For the sake of simplicity, the characterizing elements of these possible schemes of a cell are schematized, the inlets and outlets from and to the cell exterior having not been indicated.

Cells 1 and 2 are suited to the construction of a two-compartment stack, delimited by membranes of opposite sign as a repetive unit. Cell 3 is suited to the construction of a three-compartment stack, delimited by membranes of opposite sign. Cell 4 is suited to the construction of a more complex stack because of the membrane configuration, but it offers the advantage of securing a suitable conductivity even when the negatively charged species (I) have almost completely moved from compartment A to compartment B.

The process is characterized by the following electrodic reactions:

cathode: $H^+ + e^- \rightarrow \frac{1}{2} H_2$
anode: $\frac{1}{2} H_2O \rightarrow \frac{1}{4} O_2 + H^+ + e^-$ As a consequence, the electrodes conventionally used in electrolytic cells may be installed. Even simpler cells, having only one membrane (M+ or M−) are possible; in this case, the starting mixture and the fractionated species (I) are directly in contact with the electrodes. Therefore the fractionation conditions must be such that the species involved are stable with regards to the electrodic reactions, i.e. towards the development of oxygen and hydrogen. The membranes which can be used in this process are for example:

MC 3470 (cation-exchange) and
MA 3475 (anion-exchange)
[Supplier CYBRON CHEM INC. (G.B.)]
or
CMT SELEMION (cation-exchange)
AMR SELEMION (anion-exchange)
[Supplier ASAHI GLASS CO. (J)]
or
CSP (cation-exchange)
ADP (anion-exchange)
[Supplier MORGANE (F)].
or
NAFION 324 (cation-exchange)
[Supplier DUPONT].

The cation-exchange membranes are permeable to the positively charged species (I) and to the inorganic cations present; the anion-exchange membranes are permeable to the negatively charged species (I) and to the inorganic anions present. Both kinds of membranes have good resistance to the operative pH values as well as mechanical and heat resistance, they are scarcely prone to clogging and they may be re-cycled after optional washings with water, with an hydroalcoholic solution, with a diluted acidic solution, with a diluted basic solution, again with water or with a saline aqueous solution according to the conventional method.

The starting concentration of the inorganic salts in the compartments ranges from 0 to 5M so as to obtain the best current density.

The process may be carried out at a current density from 20 to 3,000 A/m², referred to the surface of each installed membrane. The following examples further illustrate the invention.

EXAMPLE 1

In an electrochemical cell of composition 4)

with platinum electrodes, fitted with MA 3475 (M+) and MC 3470 (M−) membranes, using KOH as catholyte (starting concentration 0.05M) and $K_2SO_4$ as anolyte (starting concentration 0.66M), an aqueous solution of GPE/GPC of composition 50%/50%, overall purity 99.6%, and of concentration 0.1M in both species (I) was introduced into compartment A, at a pH of 9.75 obtained by means of NaOH, and a 0.1M sodium acetate and 0.1M acetic acid aqueous solution was introduced into compartment B.

The electrolysis was carried out at 3A corresponding to 300 A/m² of exposed membrane surface. After 40,000 coulombs, compartment A contained a mixture of GPE/GPC of composition 3.5%/96.5% at pH of about 13.

Compartment B contained at the end GPE, free from GPC, at a pH of about 13.

The recovery of GPC and GPE at the end of the electrodialysis was >80%.

Repeating example 1, but interrupting the electrodialysis after the use of 20,000 coulombs, the composition of compartment A was GPE/GPC 7%/93%, whereas in compartment B GPE was free from GPC.

EXAMPLE 2

In an electrochemical cell similar to that used in Example 1, an aqueous mixture of GPE/GPC 47.6%/52.4% of overall purity 90% and having total concentration 0.14M of the species (I), obtained by deacylating deoleated soy lecithin (supplier Solvay Duphar) and subsequent elution on silica according to known methods, was introduced into compartment A and an aqueous solution of 0.05M KCl was introduced into compartment B.

The electrodialysis was carried out at 0.5 A corresponding to 50 A/m² of exposed membrane surface and using a total of 8800 coulombs. Compartment A contained at the end a mixture of GPE/GPC 25%/75% at pH 12.5. The recovery of GPC and GPE at the end of the electrodialysis was >90%.

Compartment B contained an aqueous solution of GPE, free from GPC at pH 12.5.

EXAMPLE 3

In an electrochemical cell having configuration 1)

with platinum electrodes, fitted with MA 3475 membrane (M+), Nafion 324 ($M_1^-$) and Selemion CMT ($M_2^-$) membrane, an aqueous solution of NaOH (starting concentration 0.5M) was introduced as catholyte, an aqueous solution of $H_2SO_4$ 0.3M as anolyte, an aqueous solution containing GPE/GPC 35%/65% was introduced into compartment A, 0.35M $Na_2SO_4$ aqueous solution was introduced into compartment B.

Compartments A and B were alkalinized at pH 10.5 by the addition of NaOH. The electrodialysis was carried out at a variable current starting from 1A. During electrodialysis, the pH of compartments A and B was kept at 10.5±0.5 by the addition of NaOH. The final ratio between GPC and GPE in compartment A was 99.8 to 0.2, whereas in compartment B GPE was free from GPC.

EXAMPLE 4

In an electrochemical cell having configuration 1)

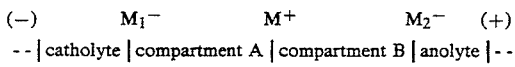

with platinum electrodes, fitted with MA 3475 membrane ($M^+$), Nafion 324 ($M_1^-$) and Selemion CMT ($M_2^-$) membrane, an aqueous solution of NaOH (starting concentration 0.5M) was introduced as catholyte, an aqueous solution of $H_2SO_4$ 0.3M as anolyte, an aqueous solution containing GPC, GPE, GPA and glycerophosphoric acid methyl ester at the ratios 59/32/4/5 was introduced into compartment A, a 0.35M $Na_2SO_4$ aqueous solution was introduced into compartment B. Compartments A and B were adjusted to pH 7.5 by the addition of NaOH.

The electrodialysis was carried out at variable current starting from 1A. In these conditions, GPA and the corresponding methyl ester were recovered in compartment B, whereas GPC and GPE remained in compartment A.

EXAMPLE 5

In an electrochemical cell having configuration 1)

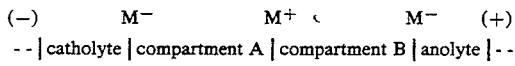

with platinum electrodes, fitted with MA 3475 ($M^+$) membrane and with MC 3470 ($M^-$) membranes, NAOH aqueous solution was introduced as catholyte (starting concentration 0.1M), a 0.05 M $H_2SO_4$ aqueous solution as anolyte, an aqueous solution containing GPC, GPE and GPA at the ratios 24/50/56 (deriving from the hydrolysis of soy lecithin with phospholipase D and subsequent deacylation) was introduced into compartment A, a 0.01M NaOH aqueous solution was introduced into compartment B. Compartments A and B were adjusted to pH 7.5 by the addition of NAOH.

The electrodialysis was carried out at the constant current of 3A. During electrodialysis the pH of compartment A was kept at the value of 7.5±0.5 by the addition of NAOH. After 8,000 coulombs compartment A contained the GPC and GPE whereas in compartment B high purity GPA was present.

Repeating Example 5 but substituting the mixture of GPC, GPE and GPA in compartment A with a mixture consisting of GPC, GPE and GPS at the ratios 34/21/45 (deriving from transphosphatidylation of soy lecithin with phospholipase D and subsequent deacylation) GPS free from GPC and GPE was recovered from compartment B.

What is claimed as new and desired to be secured by letters patent of the United Stated is:

1. A process for fractionating deacylated glycerophospholipids of formula (I)

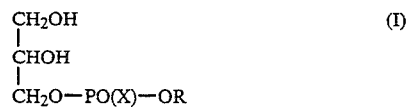

wherein
R is a negative charge, a hydrogen atom, a $CH_2CH_2NR^1R^2$ residue (wherein $R^1$ and $R^2$ which are the same or different, are H or $C_1$-$C_4$ alkyl), a $CH_2CH_2N^+(CH_3)_3$ residue, a $CH_2CH(NH_2)COOH$ residue or a residue of formula

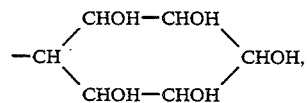

and
X is OH or $O^-$, comprising subjecting an aqueous or hydroalcoholic solution comprising two or more of said deacylated glycerophospholipids to electrodialysis in an electrolytic cell comprising a number of compartments, wherein said compartments are separated by cation-exchange membranes, anion-exchange membranes or both cation-exchange and anion-exchange membranes, at a pH effective to differentiate said deacylated glycerophospholipids.

2. The process according to claim 1, wherein said solution further comprises non-glycerophospholipidic impurities.

3. The process according to claim 1, wherein said deacylated glycerophospholipids comprise (i) a deacylated glycerophospholipid of the formula

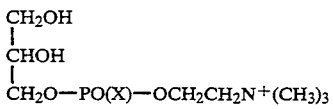

wherein X is OH or $O^-$, and (ii) a deacylated glycerophospholipid of the formula

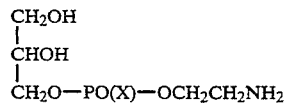

wherein X is OH or $O^-$; and said electrodialysis is conducted at a pH >8.5.

4. The process according to claim 1, wherein said electrolytic solution comprises inorganic salts, inorganic acids, inorganic bases or mixtures thereof.

5. The process according to claim 1, wherein inorganic salts are introduced during electrodialysis into said compartment containing the solution to be separated.

6. The process according to claim 5, wherein 0 to 5M inorganic salts are introduced.

7. The process according to claim 1, wherein said electrodialysis is carried out at current densities ranging from 20 to 3,000 A/$m^2$ as measured at the surface of each membrane.

8. The process according to claim 1, wherein said electrodialytic cell is composed of a series of compartments separated by cation-exchange membranes and anion-exchange membranes.

* * * * *